(12) United States Patent
Viswanathan et al.

(10) Patent No.: US 7,662,411 B2
(45) Date of Patent: Feb. 16, 2010

(54) PROCESS FOR REMOVAL OF SOLVENT AND DETERGENT FROM PLASMA

(75) Inventors: Chandra Viswanathan, Mumbai (IN); Mosuvan Kuppusamy, Mumbai (IN); Manjunath Kamath, Mumbai (IN); Vilas Baikar, Mumbai (IN); Arati Tanavade, Mumbai (IN); Narahari R. Prasad, Mumbai (IN); Ritesh Dhundi, Mumbai (IN)

(73) Assignee: Reliance Life Sciences Pvt. Ltd., Navi Mumbai, Maharashtra (IN)

( * ) Notice: Subject to any disclaimer, the term of this patent is extended or adjusted under 35 U.S.C. 154(b) by 330 days.

(21) Appl. No.: 11/171,877

(22) Filed: Jun. 29, 2005

(65) Prior Publication Data

US 2006/0008792 A1 Jan. 12, 2006

(51) Int. Cl.
*A61K 35/16* (2006.01)
(52) U.S. Cl. .................................................... 424/530
(58) Field of Classification Search ................ None
See application file for complete search history.

(56) References Cited

U.S. PATENT DOCUMENTS

| 4,314,997 A | 2/1982 | Shanbrom |
| 4,540,573 A | 9/1985 | Neurath et al. |
| 5,094,960 A * | 3/1992 | Bonomo ..................... 436/178 |
| 5,817,765 A | 10/1998 | Isaksson et al. |
| 5,834,420 A | 11/1998 | Laub et al. |
| 6,610,316 B2 | 8/2003 | Shanbrom |

FOREIGN PATENT DOCUMENTS

| CN | 1371992 A | 10/2002 |

OTHER PUBLICATIONS http://hplc.chem.shu.edu/NEW/HPLC-Book/glossary/df-poly.html, definition of polystyrene-divinylbenzene resin (PS-DVB), accessed Dec. 18, 2007.*
Strancar et al., "Extraction of Triton X-100 and its determination in virus-inactivated human plasma by the solvent-detergent method", J. Chromatography A, 658 : 475-481 (1994).*
Majors et al., "Glossary of Liquid-Phase Separation Terms", LCGC 19 (2) : 124,126,128,130,132,134,136,138,140,142,144,146, 148,150,152,154,156,158,162 (2001).*
Stolker, "Current Trends and Developments in Sample Preparation", Euroresidue IV, Veldhoven, NL, May 8-10, 2001, pp. 148-158.*
Diaion (R) & Sepabeads (R), http://www.diaion.com, online catalog, accessed Dec. 18, 2007.*
Jackson, B. et al. (Jul. 28, 1999). "Update of Cost-Effectiveness Analysis for Solvent-Detergent-Treated Plasma," *Journal of the American Medical Association* 282(4):329.
Nellaiappan, K. et al. (Jun. 5, 2001). "Validation of a Simple and Sensitive Gas Chromatographic Method of the Analysis of Tri-N-Butyl Phosphate From Virally Inactivated Human Immunoglobulin," *Journal of Chromatography B* 757(1):181-189.
Seitz, H. et al. (Sep. 2002). "Comparable Virus Inactivation by Bovine Derived or Vegetable Tween 80 During Solvent/Detergent Treatment," *Biologicals* 30(3):197-205.

* cited by examiner

*Primary Examiner*—Sandra E Saucier
(74) *Attorney, Agent, or Firm*—Mintz, Levin, Cohn, Ferris, Glovsky and Popeo, P.C.

(57) ABSTRACT

The present invention relates to a process of disinfecting biological materials. In particular, a novel process is provided for removing detergent and/or solvent added to biological materials for the inactivation of viral contaminants. Safe, efficient, and economical methods for removing virucidal agents such as solvent-detergent from virus-inactivated pooled plasma by hydrophobic interaction chromatography are provided. Methods for clearing solvent-detergent from virus-inactivated biological materials in a single step are also provided.

20 Claims, 1 Drawing Sheet

PROCESS FOR REMOVAL OF SOLVENT AND DETERGENT FROM PLASMA

CROSS-REFERENCE TO RELATED APPLICATIONS

This application claims priority from Indian provisional patent Application No. 695/MUM/2004, filed Jun. 29, 2004.

TECHNICAL FIELD OF THE INVENTION

The present invention relates to processes for safe removal of virucidal materials from biological samples. In particular, the invention relates to processes for removal of detergents and/or solvents from biological materials.

BACKGROUND OF THE INVENTION

Human plasma serves as a source for deriving valuable proteins. Therapeutic proteins derived from human plasma have been used in the treatment of a broad range of diseases including primary immune deficiencies (immunoglobulin G), critical care involving hypovolemia (albumin), wound healing (fibrinogen), and hereditary deficiencies such as hemophilia A (Factor VIII), hemophilia B (Factor IX), von Willebrand's disease (vWF), and congenital emphysema resulting from a deficiency of alpha-1 Proteinase Inhibitor (A1PI). Besides its application as a raw material for isolating very valuable proteins, whole human plasma continues to be major source of coagulation factor replacement therapy for patients with clotting factor deficiency. Human plasma and therapeutic proteins derived therefrom are used to treat about more than one million patients globally each year. The global demand of such therapeutics is significantly greater than the current level of supply.

For patients in the need of whole plasma for therapeutic purposes, it is available as either fresh frozen plasma or liquid plasma. Fresh frozen plasma (FFP) is the plasma removed from a unit of whole blood and frozen at or below −18° C. within eight hours of blood collection as a single-donor plasma unit. Liquid plasma is stored at temperatures of 4-8° C. within 4 hours of blood collection and separated from the red blood within 48 hours of blood collection. Each of these plasma units are from single donors and individually tested for viral markers and, in regards to viral transmittance, single donors are considered to be reasonably safe. However, there continues to be a small but defined risk of viral transmission, because such plasma units usually do not undergo a process of viral inactivation to kill viruses like HIV, hepatitis B, hepatitis C, and other viruses which could potentially cause disease.

For the purpose of deriving the therapeutic proteins, a large number of fresh frozen plasma units are pooled together from various donors. Human plasma proteins for therapeutic use have been manufactured from large pools of plasma for over 50 years. One of the important concerns of single donor or pooled plasma, however, is viral safety. Though every donor who contributes to the pool of plasma is tested individually for viruses, including HIV, HBV, HCV, etc. before blood or plasma donation, there remains a small risk of infection with viruses due to "window period donations," that is donations made between the initial acquisition of infection and the detection of a positive test result with existing diagnostics due to inherent technical limitations. Even a single donor infected with a pathogen, which remained undetected after screening, can potentially contaminate an entire pool of plasma and infect many or all recipients exposed to the pool. Therefore, there is a need to address the viral safety of pooled plasma or the therapeutic proteins derived therefrom.

To render plasma or plasma-derived therapeutic proteins virus-safe, various methods have been attempted to remove or inactivate viruses. For virus inactivation, biological fluids of interest are subjected to physical treatments like pasteurization, wherein the pooled plasma is subjected to wet heat at a temperature of about 60° C. for periods of about 10 hours, or treated with dry heat during which the product of interest is treated at higher temperature of about 80° C. for prolonged periods as long as about 72 hours. Such treatments often are found to damage, denature, or vary valuable protein factors, especially labile blood-coagulating components under conditions to which the biological samples are subjected for inactivating the viruses efficiently. During such inactivation processes, the labile coagulation components of the mammalian blood plasma may get inactivated or denatured as much as up to the extent of 50-90% or more present in the untreated plasma. The coagulating components which may be lost during such treatment include valuable plasma factors like factors II, VII, IX, X; plasma fibrinogen (factor I), IgM, hemoglobin, interferon, etc. Therefore, attempts have been made to incorporate steps suitable for protecting proteins of interest.

Other methods for viral inactivation involve treatment with β-propiolactone, formaldehyde, sodium hypochlorite, and the like. However, these methods are generally not considered to be very safe. These methods not only tend to denature the valuable protein components, but also pose difficulties in complete removal of agents such as β-propiolactone which is deleterious and has shown to be carcinogenic in animals and is dangerous even to personnel handling it.

One of the most commonly employed methods for viral inactivation of plasma or plasma derived protein products is solvent detergent treatment. Solvent detergent treated plasma has been approved for use in the treatment of patients with documented deficiencies of coagulation factors for which there are no concentrate preparations available, including congenital single-factor deficiencies of factors I, V, VII, XI and XIII, and acquired multiple coagulation factor deficiencies; reversals of warfarin effect; and treatment of patients with thrombotic thrombocytopenic purpura (TTP). A cost-effectiveness analysis for solvent-detergent-treated frozen plasma (SDFP), calculated a cost of $289,300 per quality-adjusted life year (QALY) saved. (Jackson et al. JAMA.1999; 282: 329). Solvent-detergent treatment is particularly effective for enveloped viruses such as Vesicular Stomatitis Virus (VSV), Pseudorabiesvirus (PRV), Semliki Forest Virus (SFV) and Bovine Diarrhoea Virus (BVDV). (Seitz et al. Biologicals, 30(3): 197-205(9) (2002)). Solvent detergent treatment is primarily employed to reduce the already-low risk of viral transmitted fresh frozen plasma from donors in the infectious, seronegative window period of currently known viral infections and the risk of transmission of lipid enveloped viruses not currently recognized as a risk to transfusion safety may very well could still be a potential risk in the future.

In a solvent detergent treatment for virus inactivation, the protein-containing composition is contacted with dialkyl- or trialkylphosphate, preferably with mixtures of trialkylphosphate, and detergent, usually followed by removal of the dialkyl- or trialkylphosphate (see U.S. Pat. No. 4,540,573). The '573 patent employed dialkyl- or trialkylphosphate in an amount between about 0.01 mg/ml and about 100 mg/l. The amount of detergent employed, according to the '573 patent, could range from about 0.001% to about 10%. Similarly, U.S. Pat. No. 4,314,997 employed a detergent concentration could vary from 0.25% to as high as about 10%.

Another detergent approach of viral inactivation is to subjecting plasma protein products to prolonged contact with non-denaturing amphiphile (see U.S. Pat. No. 4,314,997). Amphiphiles can be anionic, cationic, nonionic detergents. The amphiphilic detergent molecule is hydrophobic at one end and hydrophilic at the other end, which makes it useful for purification of therapeutic blood proteins. Ionic detergents, either anionic or cationic tend to more active than nonionic detergents. While being effective at destroying viruses, detergents may readily destroy or damage living cells. Detergents are capable not only of destroying viruses, but also disrupting other vital lipid-based structure like biomembranes that surrounds and form a significant internal structural component of every animal and plant cell. Further, high concentrations of detergent are likely to damage or denature proteins that are present and/or desirable for isolation from the biological sample. The incubation of plasma, plasma derived therapeutic proteins, plasma cryoprecipitate, or plasma cryosupernatants with such high concentration of the detergents not only would harm the plasma components but also are known to damage biomembranes. Moreover, the high concentration of detergent is extremely harmful when injected intravenously and hence such detergent-treated plasma would not be suitable for injections. To avoid damage to living cells and proteins, a lower concentration of detergent can be employed, but at the risk of being ineffective for viral inactivation. Therefore, to ensure living cells and proteins are not damaged and at the same time viral inactivation is effective, removal of detergents is imperative.

Commonly employed methods for removal of detergent include affinity or ion-exchange chromatography. These methods are lengthy and time consuming, and involve multiple steps. As one skilled in the art would appreciate, each recovery step is often associated with the loss of proteins of interest and hence result in lower yield. Further, these methods are suitable only for the particular protein factor as an end product and would not be appropriate for the whole plasma. To make it applicable to whole plasma, whole plasma would need to be reconstituted after each of the factors is successively separated and purified. After each step, some amount of time and product would be lost, which may ultimately lead to significant overall loss.

After solvent-detergent treatment, the detergent can be removed by employing several steps chosen among diafiltration, adsorption on chromatographic or affinity chromatographic supports, precipitation and lyophilization, etc. Dialkyl- or trialkylphosphate is often removed by precipitation of the protein with glycine and sodium chloride (see U.S. Pat. No. 4,540,573). The process of the '573 patent is particularly time-consuming as nonionic detergents employed with the trialkylphosphate are removed by diafiltration using either insolubilization or lyophilization. One skilled in the art appreciates that these processes are cumbersome, expensive, time consuming, and/or can result in loss of vital components of plasma.

Removal of detergent and solvent can additionally be preformed by partitioning the protein solution against an organic liquid such as castor or soy bean oil. The detergent and solvent partition into the organic liquid and are thus eliminated. The organic liquid that is oil is then removed by chromatography. This procedure involves partitioning of plasma and regenerating or replacing the chromatographic components, which tend to be very tedious, time consuming and cost intensive.

Another method for reducing of virus-inactivating chemicals and/or detergent is by high salting out effect (see U.S. Pat. No. 5,817,765). In this procedure, a concentration above 0.5M of salt with high salting out effect according to Hofmeister series is added to the aqueous plasma protein solution for forming vesicles containing the virus-inactivating chemicals and/or detergents. The vesicles are removed from the aqueous phase, for example by phase separation or filtration. The technique of phase separation, however, particularly that of vesicles, is laborious, imprecise, and difficult method, which would be very cumbersome in large scale operations because of operational issues like cleaning, sanitization, process validation, etc. Additionally, the further step of protein recovery from aqueous solution may result in the loss of final protein yield. Any trace of salt remaining in the plasma product, would also be undesirable as it would render it unsuitable for the most therapeutic applications.

Removal of solvent/detergent can alternatively be performed by using carbon either in the form of activated carbon or charcoal. For example, Chinese Patent number CN 1371992 employs solid phase material containing active carbon as adsorbent for removing organic solvent used as virus inactivator and/or detergent from aqueous solution. U.S. Pat. No. 5,834,420 uses precipitation of viral inactivated fraction in a solution containing an amino acid at an acidic pH and filtering. Preferably the filtration step is carried out through a filter of activated carbon of which AKS-4 and AKS-7 are particularly suited. Carbon, however, is a nonspecific adsorbent, and when employed to adsorb virus inactivator and/or detergent, may also adsorb some of the important peptides components of interest from the plasma. The use of carbon could result in a final product devoid of these useful components.

U.S. Pat. No. 6,610,316 discloses a "sugar detergent" rendered insoluble by being bound to an inert substrate. The method described in the '316 patent requires an additional step of binding the detergent to the resin. Further, additional testing protocol could be required to check or ensure sufficient binding of the detergent in order to avoid leaching of the detergent into the blood solution. Detergent that is not bound sufficiently to the resin could contaminate the blood product and render it unsafe for the desired use. Further, the method disclosed in the '316 patent is directed to blood or aqueous liquid containing blood cells, and does not demonstrate the suitability of this method for plasma or plasma derived proteins.

From the forgoing reasons, it is evident that it is imperative to treat plasma or plasma derivatives with virus-inactivating agents to render it safe for therapeutic applications. It is also important to improve such virus-safe plasma or plasma derivatives by clearing the virucidal agents employed for inactivating viruses to desired acceptable level for clinical use. However in view of the drawbacks associated with the methods discussed above, there continues to exist a need for providing a simple, reproducible process, not compromising time consumed and yield, yet easily validated for improving virus-safe biological fluids including plasma or plasma derivatives by clearing virucidal agents like detergent and solvent to acceptable levels using effective and simple methods without significantly affecting the plasma composition.

SUMMARY OF THE INVENTION

The present invention provides a process for improvement of virus-safe biological materials including, but not limited to plasma, plasma derived proteins, plasma cryoprecipitates, plasma cryosupernatants, blood products and any other biological fluid by clearance of the virucidal agents to the desired level and/or pharmaceutically acceptable level.

It is also an aspect of the present invention to provide a simple, yet effective process for improvement of virus-safe biological materials by clearance of virucidal agents to a desired level and/or a pharmaceutically acceptable level, in a single step.

The present invention also relates to a process for improvement of virus-safe biological materials by clearance of virucidal agents to desired levels, wherein the process does not substantially damage the labile components of the plasma or biological fluids.

The present invention also relates to a present invention to provide the process for improvement of virus-safe biological materials by clearance of virucidal agents to desired level and/or pharmaceutically acceptable level, applicable to laboratory scale.

The present invention also relates to a process for improvement of virus-safe biological materials by clearance of virucidal agents to a desired level and/or pharmaceutically acceptable level, suitable for commercial large-scale manufacturing.

The present invention also relates to a process for improvement of virus-safe biological materials by clearance of virucidal agents to a desired level and/or pharmaceutically acceptable level, wherein the method is easily validated and reproducible.

The present invention also relates to a process for improvement of virus-safe biological materials by clearance of virucidal agents to a desired level and/or pharmaceutically acceptable level as recommended in official pharmacopeia monographs, to make the biological fluid acceptable for therapeutic clinical administration.

The present invention also relates to a process for improvement of virus-safe biological materials by clearance of virucidal agents to a desired level and/or pharmaceutically acceptable level by methods suitable for the said purpose.

The present invention also relates to a process for preparing improved virus-safe biological materials by clearance of virucidal agents to a desired and/or pharmaceutically acceptable level using methods and materials, which do not leach in the product solution and thus reduce the risk of contamination by such agent.

The present invention also relates to a process for preparing improved virus-safe biological materials by clearance of virucidal agents to a desired and/or pharmaceutically acceptable level using methods that are reusable with different batches of biological material for said purpose.

The present invention also relates to a process for preparing improved virus-safe biological materials by clearance of virucidal agents to a desired and/or pharmaceutically acceptable level using methods that do not alter significantly the composition of plasma or biological materials and thereby substantially preserve the original composition.

DETAILED DESCRIPTION OF PREFERRED EMBODIMENTS

Figure 1:
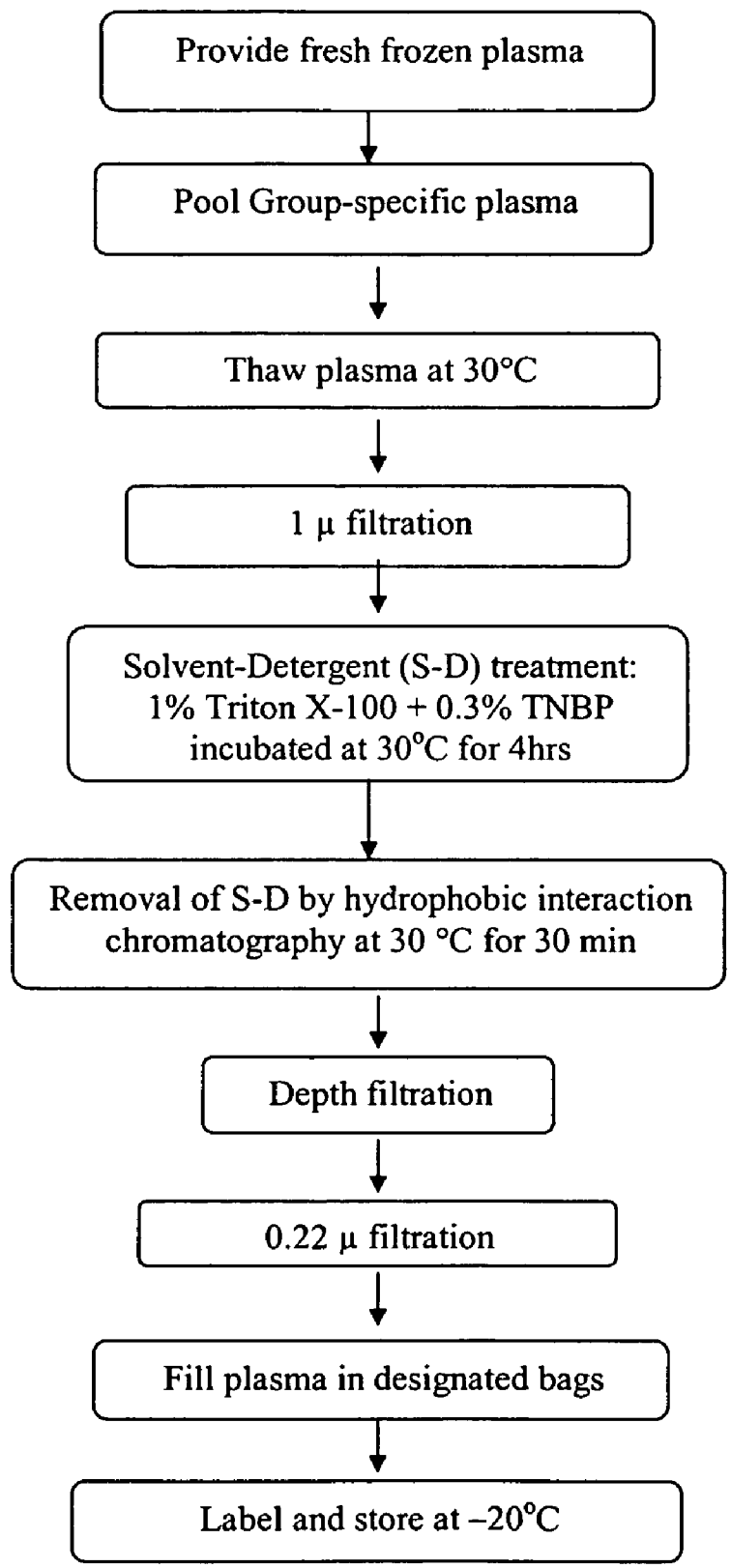
FIG. 1 depicts a flow chart of an example of processing of a 5 liter batch of plasma, according to the invention.

The present invention provides novel processes for removal and/or inactivation of virucidal agents used to remove viral contaminants from biological materials.

Definitions

As used herein, "virus-safe" for the purpose of the present invention refers to any biological material, which has undergone virus inactivation treatment, such as biological fluid with solvent and/or detergent to substantially inactivate viruses. In some embodiments, substantial inactivation is obtained to the extent of at least "4 logs," i.e., virus is inactivated to the extent determined by infectivity studies where the virus was present in the untreated serum in such a concentration that even after dilution to $10^4$ viral activity can be measured. Alternatively, substantial inactivation is obtained by a process which, when challenged with 6 logs of virus ($10^6$ infective units) less than two logs of virus is recovered following completion of the process.

As used herein, "virucidal agent(s)" for the purpose of present the invention refers to any agent like solvent, detergent and/or combinations thereof, which has ability to substantially inactivate viruses, particularly lipid-coated or enveloped viruses from biological material.

As used herein, "clearance" for the purpose of the present invention refers to removal or reduction of the virucidal agents.

The present invention relates to a novel process to remove viral contaminants from biological materials to create virus-safe biological materials by clearance of virucidal agents to a desired level and/or pharmaceutically acceptable level.

The present invention relates to a process for removal of virus-inactivating agents used against lipid-coated viruses including, but not limited to HIV, hepatitis B and hepatitis C viruses, as well as other viruses including, but not limited to cytomegalovirus, Epstein Barr virus, lactic dehydrogenase-elevating viruses (e.g., arterivirus), herpes group viruses, rhabdoviruses, leukoviruses, myxoviruses, alphaviruses, Arboviruses (group B), paramyxoviruses, arenaviruses, and coronaviruses.

In one embodiment, the biological materials that can be processed in accordance with the present invention include, but are not limited to plasma, plasma concentrate, plasma derived proteins, plasma cryoprecipitate, plasma supernatant, vaccine, blood product or any such biological fluid.

In another embodiment, the process is used in treating solid components of blood, lysates, or proteins secreted by cells. Thus, also contemplated are treatment of platelet concentrates, white cell (leukocyte) concentrates, and leukocyte-poor packed red cells as well as platelet-rich plasma, platelet concentrates, and platelet-poor plasma including packed cell masses comprising white buffy coat consisting of white blood cells above packed red cells. Also contemplated is the treatment of masses containing concentrates of granulocytes, monocytes, interferon, and transfer factor.

In another embodiment, the process is used in inactivating virus present in products of normal or cancerous cells. For instance, by the same treatment, one can inactivate virus present in products produced using normal or cancer cells, the exudates from normal or cancerous cells, hybridomas and products produced by gene splicing. Cells used for production of desired product can be mammalian as well as non-mammalian.

It is an embodiment of the present invention to provide a process for making plasma substantially free from solvent-detergent and not substantially alter vital components of the plasma. Vital components include, but are not limited to fibrinogen, factor VIII, properdin, IgG, IgM, IgA, beta-lipoprotein, prothrombin, plasminogen, plasmin inhibitor, thrombin, isoagglutinins, factor V, factor VII, factor IX, factor X, cerutoplasmin, alpha- and beta-globulins, albumin, alpha-1-proteinase inhibitor, vWF, alpha-1-lipoprotein, transferring, and thyroxine binding globulin.

Pooled plasma either to be used for patients in the need of coagulation factor therapy or to serve as a source for therapeutic protein factors therefrom is commonly subjected to treatment with virucidal agents like solvent detergent to inactivate viruses and render the plasma virus-safe for clinical applications or improve the safety profile of the coagulation factors derived therefrom. However in view of the deleterious effect of the solvent detergent they are required to be eliminated from the virus-safe biological fluids to the acceptable levels. A pharmaceutically acceptable amount in the final product is less than 2 mcg/ml for tri-n-butyl phosphate and less than 5 mcg/ml for Triton®-X 100.

One embodiment of the invention provides a process for clearance of virucidal agents to a desired level and/or pharmaceutically acceptable level as laid down in official pharmacopeia and thereby improving its clinical profile. Guidelines promulgated by the U.S. Food and Drug Administration can be accessed over the internet at www.fda.gov/cber/guidelines.htm. The present invention novel process for clearance of virucidal agents is a single step, simple and rapid process unlike the hitherto disclosed methods for the same intent. Other advantageous features of the processes of the present invention process are that they can be conveniently validated and are reproducible.

The present invention can be employed to prepare virus-safe plasma, plasma concentrate, plasma derived proteins, plasma cryoprecipitate, plasma supernatant, blood product or any such biological fluid already treated with virucidal agents or it can be employed after subjecting the said biological fluid to virus inactivating treatment to render them virus-safe.

For inactivation of virus, biological fluid is subjected to treatment with virucidal agents like solvent and/or detergent.

The solvents that may be employed as virucidal agent can be selected from dialkyl- or trialkyl phosphates having branched or unbranched, substituted or unsubstituted alkyl groups, suitably with 1 to 10 carbon atoms or combination thereof. Mixtures of various dialkyl phosphates can also be used, as well as mixtures of various trialkyl phosphates. Mixtures of dialkyl and trialkyl phosphates are also within the scope of the present invention. The tri-alkyl phosphates that may be employed can be selected from those wherein the alkyl group is n-butyl, t-butyl, n-hexyl, 2-ethylhexyl and n-decyl or combinations thereof. A suitable virus-inactivating solvent is tri-n-butyl phosphate (TNBP).

Detergents that can be employed as virucidal agents include a non-ionic detergent, such as a polyoxyethylene ether, e.g. a TRITON®, or a polyoxyethylene sorbitan fatty acid ester, such as polyoxyethylene-(20)-sorbitan monolaurate or polyoxyethylene-(20)-sorbitan monooleate, sodium deoxycholate, synthetic zwitterionic detergent known as "sulfobetaines" such as N-dodecyl-N,N-methyl-2-ammonio-1 ethane sulphonate and its congeners or nonionic detergent such as octyl-β-D-glucopyranoside. One suitable detergent is TRITON® X-100.

The virus inactivation treatment involves addition of virucidal agents that are solvents and detergents to the aqueous solution of interest. The amount of solvent and detergent varies depending on the volume of solution to be treated. In one embodiment, solvent can be employed up to a concentration of about 2 percent weight by weight. In one embodiment, the detergent can be added up to a concentration of about 2 percent weight by weight. In some embodiments, the virus inactivation treatment can be carried out for about 1 hour to about 16 hours, at temperatures ranging from about 4° C. to about 50° C.

In accordance with the present invention the virus-safe biological fluid, which has undergone virus inactivation treatment by virucidal agents, is subjected to a single step of clearance of the virucidal agents. Surprisingly it was discovered by the inventors that it was possible to remove both the detergent as well as solvent by employing a single step of clearance as disclosed the present invention.

In an embodiment of the present invention, material such as organic matrix is employed to clear virucidal agents. The biological fluid is contacted with organic matrix with a sufficient surface area for a limited period of time. The virucidal agent gets physically adsorbed on the surface of organic matrix and the separation of supernatant produces biological fluid with virucidal agents eliminated to a significant level.

The process of clearance of virucidal agents can be successfully employed at laboratory as well as commercial production levels. FIG. 1 illustrates one example of a manufacturing process for clearing virucidal agents. Further the process can be carried out in either a batch mode or a column mode.

In one embodiment of the present invention process clearance of virucidal agents in a batch mode is carried out in a vessel wherein the virus-safe biological fluid, with virucidal agents remaining therein after virus inactivation treatment, is contacted with organic matrix in a predefined ratio, under stirring, at a temperature of about 10-40° C., preferably 18-30° C. for a period of about 0.1 hour to 4 hours, preferably between about 0.15 hr. to about 2 hrs. The supernatant is separated from the organic matrix by removal of organic matrix by employing by any suitable technique like simple filtration, filtration under vacuum, centrifugation or any suitable technique. The virucidal agents, which get physically adsorbed on the organic matrix, are eliminated to a significant level from the biological fluid.

In another embodiment of the present invention process the clearance of virucidal agents in a column mode, is carried out in a column pre-packed with organic matrix, through which the biological fluid contaminated with the virucidal agents is passed. The contact time between the biological fluid of interest and organic resin is adjusted so as to range from about 0.1 hr-4 hrs, preferably from about 0.15 hr. to 2 hrs. A column, which can be employed for that purpose, is 1-25 cm, preferably 4-16 cm, in height and the diameter of which can be adjusted according to the volume of the biological fluid to be treated.

The organic matrix to be employed for the purpose of the present invention for the clearance of virucidal agents is selected from synthetic polymers, which are polyaromatic or methacrylate based resins, and which generally do not have tendency to leach in the solution undergoing treatment. The polyaromatic resins of the present invention are selected from the class of polystyrene-divinylbenzene copolymer resins with grades preferably having higher surface area. The polystyrene-divinylbenzene copolymer resin can be selected from DIAION® HP20, DIAION® HP20 SS, SEPABEADS® SP825, etc. (Mitsubishi Chemical Corp., Tokyo, Japan). The methacrylate-based resins can be selected from DIAION® HP2MG, SEPABEADS® SP70, SEPABEADS® SP207, etc. (Mitsubishi Chemical Corp., Tokyo, Japan). Alternatively any other adsorbent matrix can be employed for the purpose of present invention having the ability to sufficiently adsorb the virus inactivating agents Following use in removal of solvent-detergent, the organic matrix can be reused with different batches, after regenerating and sanitizing.

The ratio of resin to the virus-safe biological fluid to be treated can vary between 1:1 to 1:40, preferably between 1:2 to 1:25, and more preferably between 1:3 to 1:10.

The process for improvement of virus-safe biological fluids by clearance of virucidal agents can be effectively employed both for single component protein derived from the plasma or to the whole plasma it self either a single unit fresh frozen plasma unit or pooled plasma useful for patients with deficiency of coagulation factors, deficiency of acquired multiple coagulation factors, also in patients needing reversal of warfarin effects, thromocytopenia, long prothrombin time, head injuries, joint bleeds, dental bleeds, subdural hematoma, hematuria, gastro intestinal bleeding, hemoperitoneum, or any such like disorder.

The process when employed for virus-safe plasma does not alter the vital components of the plasma. Thus, the composition of the plasma processed in accordance with the present invention is almost like the original plasma. Accordingly the improved viral safe plasma obtained as a result of the present invention process may have lower levels of immunogenicity, as highly conserved proteins tend to have rather low immunogenicity and hence therapeutically more useful.

It is to be understood by those skilled in the art that the foregoing specification is to indicate the nature of the invention which is non limiting and the present invention may be embodied in the specific forms without departing from the spirit or attributes thereof and various modifications and changes may be made without departing from the scope of the present invention.

The removal of solvent-detergent from viral inactivated pooled plasma is illustrated in the examples set forth and the compiled tabulated data reflect the procedure for selecting the most beneficial and preferred compounds.

The following details of the studies conducted exemplify the process of invention without limiting the scope thereof.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Virus Inactivation and Removal of Solvent-detergent

Step 1: Virus Inactivation by Solvent-detergent

The plasma of donors of specific group are tested, taken from −20° C. freezer and thawed at 30° C. in water bath. The plasma is then pooled after thawing and filtered through a glass fiber filter with binder resin such as Type AP25 (Millipore Corp., Billerica, Mass., USA)

The pooled plasma is then treated with solvent tri-(n-butyl) phosphate (TNBP) and the detergent Triton® X-100 for 4 hours at 30° C. This type of detergent and solvent is known to inactivate enveloped viruses including HIV, HBV and HCV.

This type of virus inactivation by above mentioned solvent and detergent is a well-known process (see U.S. Pat. No. 4,540,573).

Step 2: Solvent Detergent Removal by Synthetic Polymer Resin

Unlike pre-existing technologies, which employ expensive, time consuming processes for removal of solvent and detergent from virus-inactivated plasma of step 1, the process of this invention is carried out by hydrophobic interaction chromatography using a synthetic polymer, typically in a single step.

The synthetic polymers are selected from the class of polystyrene based divinyl copolymers. These polymers which are highly porous and hydrophobic in nature are specifically available from the Mitsubishi Chemical Corporation (Japan) under the name of SEPABEADS® with different grades available, such as SP70, HS20 SS, SP 825, SP850, SP207 and the like. (Itochu Chemicals America, Inc., White Plains, N.Y.)

The resin, for example SP 825, is activated and equilibrated by standard procedures.

1 g of resin is added for 4 ml of solvent detergent treated plasma i.e. 1:4 (w/v) and stirred gently for 30 minutes at 30° C. The resin is separated using muslin cloth and the plasma is collected separately.

The plasma, which is now substantially free of solvent and detergent, is then passed through a Depth filter (Microfilt, India) and then through a 0.22µ filter.

The final product obtained thus complies with the specifications in the official British Pharmacopeia for Virus Inactivated pooled Plasma product wherein the maximum accepted limits of Triton® X-100 is 5 ppm and tri(n-butyl) phosphate is 2 ppm. (see The British Pharmacopeia, H.M. Printing Office, London)

Example 2

Analysis of Effect of Resin on Detergent and Factor VIII Levels

A study on various proportions of the resins and the resultant Factor VIII content and residual detergent (in ppm) is tabulated below:

TABLE 1

| Resin | Ratio | Time | Temp. | Triton (ppm) | Factor VIII (IU/ml) |
| --- | --- | --- | --- | --- | --- |
| Plasma |  |  |  |  | 0.9 |
| HP20 | 1:4 | 30 min | 4° C. | 44 | 0.82 |
| SP207 | 1:6 | 30 min | 4° C. | 25 | 0.65 |
| HP2MG | 1:8 | 30 min | 4° C. | 15 | 0.51 |
| SP70 | 1:4 | 30 min | 4° C. | 5 | 0.72 |
| SP825 | 1:4 | 30 min | 4° C. | 6.16 | 0.82 |

It was found that Triton is more than acceptable limits in HP20, SP207 and HP2MG. SP70 and SP825 removed Triton more effectively to below acceptable limits of 5 ppm. Further SP825 resin was effective in removing detergent with good recovery of Factor VIII and without any loss/inactivation of coagulation factors.

Example 3

Optimization of Temperature for Solvent-detergent Removal and Analysis of Factor VIII Levels Using SP825 Resin Extensive studies were done on SP825 for optimizing the process parameters like temperature and proportion of the resin with respect to plasma.

TABLE 2

| Resin (SP825):plasma | Time (min.) | Temp. (° C.) | Factor VIII (IU/ml) | Triton (ppm) |
|---|---|---|---|---|
| Plasma alone | | | 0.83 | 0 |
| 1:4 | 30 | 30 | 0.83 | 3.7 |
| 1:4 | 30 | 4 | 0.74 | 6.1 |
| 1:6 | 60 | 30 | 0.83 | 4.2 |
| 1:6 | 60 | 4 | 0.73 | 13.7 |

The ratio of resin to plasma in the proportion of 1:4 at 30° C. gave acceptable results for Factor VIII and Triton. However at 4° C. it was found that residual detergent was more than 5 ppm and the recovery of Factor VIII was less.

Hence, it was inferred that the most preferred temperature was room temperature in the range of 20-30° C. for effective removal of solvent and detergent.

Example 4

Optimization of Contact Time of Sample with Resin for Effective Removal of Solvent-detergent The different interval of time of contact of plasma with resin was studied for effective removal of detergent.

TABLE 3

| Resin (SP825):plasma (g:ml) | Temp. (° C.) | Resin Contact Time (min.) | Residual Triton (ppm) |
|---|---|---|---|
| 1:4 | 30 | 10 | 8 |
| 1:4 | 30 | 20 | 6 |
| 1:4 | 30 | 30 | 0.45 |
| 1:4 | 30 | 40 | 0.38 |

A proportion of 1:4 of resin to plasma at 30° C. for 30-40 minutes was optimum for removal of solvent detergent.

Example 5

Analysis of Effect of Resin on pH

There is no significant alteration of pH after treatment with resin as illustrated by experimental evidence below:

TABLE 4

| Sample | pH before Resin treatment | pH after resin treatment |
|---|---|---|
| S-D Plasma | 6.7 | 6.8 |
| S-D Plasma | 7.0 | 7.05 |
| S-D Plasma | 7.2 | 7.15 |

Example 6

Removal of Solvent-detergent by Column Mode

The performance of the resin in column and in batch modes was studied by the following procedure:
1. 10 gm of resin was weighed and packed in a XK 16 column. (Amersham Biosciences, GE Healthcare, UK)
2. 10 gm of resin was weighed and placed in a glass beaker.
3. 40 ml of solvent detergent (S-D) treated plasma was added to the resin in beaker for batch mode.
4. 40 ml of S-D treated plasma passed through the column at room temperature for column mode.
5. Flow rate was checked with the help of measuring cylinder. Typically, the flow rate was about 2.5 ml/min
6. Linear flow rate was about 75 cm/hr.
7. S-D treated plasma was passed five times through the column and a sample was collected at every pass for analysis.

TABLE 5

| Sample | Mode | Triton ppm |
|---|---|---|
| 1st pass | Column | 3.89 |

Solvent and detergent can be removed by column mode with a flow rate of 45-75 cm/hr, preferably 60 cm/hr of linear flow rate at a temperature in the range of 20-30° C.

Example 7

Regeneration of the Resin

The resin can be regenerated after every run using the following procedure described by the manufacturer. (DI-AION data sheet; Mitsubishi Chemical Corp. Japan)

The resin is washed twice with water for injection to remove any remaining plasma.

Then the resin is treated with three volumes of 3% sodium hydroxide solution for 15 minutes with slow stirring at 25-30° C., then decanted and washed with three volumes of water.

After complete removal of water, the resin is treated with three volumes of 80% isopropanol and then finally stored at room temperature.

Samples of the resin are then analyzed for isopropanol and protein by measuring optical density at 280 nm.

This regenerated resin can be reused only after extensive cleaning, validation and regulatory approval.

Example 8

Manufacturing Process on a Pilot Scale of 5 Liters

The manufacturing process involves the following steps exemplified in the flow diagram shown in FIG. 1:

Plasma frozen within 15 hours of collection from volunteer donors was debagged, pooled and thawed at a temperature not to exceed 35° C. The product underwent 1.0 µm filtration and was transferred to a process tank. The adjusted pooled plasma was virus-inactivated by the addition of 0.3% TNBP and 1% Triton X-100. The mixture was incubated at 30±2° C. for four hours. TNBP and Triton X-100 were removed by hydrophobic interaction chromatography at 20-30° C. for 30 min. followed by depth filtration and 0.22% filtration. The product was then filled in a designated bag, labeled and stored at −20° C.

The results of a scale up of laboratory scale to pilot scale using the above resins for solvent detergent removal is given below indicating the industrial applicability of this process.

TABLE 6

| Batch | Blood Group | Vol (ml) | Triton (ppm) | TNBP (ppm) |
|---|---|---|---|---|
| Pool | B +ve | 100 | | |
| 1 | B +ve | 100 | 0.48 | |
| 2 | B +ve | 100 | 0.55 | |
| 3 | B +ve | 100 | 0.53 | |

TABLE 6-continued

| Batch | Blood Group | Vol (ml) | Triton (ppm) | TNBP (ppm) |
|---|---|---|---|---|
| Pool 1 | B +ve | 1000 | | |
| 1 | B +ve | 1000 | 1.24 | below detectable limits |
| Pool 2 | O +ve | 1000 | | |
| 2 | O +ve | 1000 | 0.59 | 0.44 |
| Pool 3 | A +ve | 1000 | | |
| 3 | A +ve | 1000 | 0.81 | below detectable limits |

Example 9

Analytical Procedures for Triton and Tri-(N-Butyl) Phosphate (a) Sample Preparation for Residual Triton Analysis:

S-D treated plasma after HIC resin treatment was extracted on a C-18 cartridge with 75% isopropanol (v/v). Extraction procedure was checked by spiking known amount of Triton® X-100 in the sample. Almost 99% of the Triton® was recovered.

(b) Method of HPLC Analysis:

The extracted sample was loaded on a C-8 column and a UV detector set at 280 nm was used to detect the residual Triton®.

(c) Sample Preparation for tri(n-butyl) Phosphate:

Final sample was then extracted with hexane. Ethanol was added to get a clear supernatant. 1 µl of sample of supernatant was used for gas chromatography analysis. Extraction procedure was monitored by spiking the sample with a known amount of TNBP and recovering almost 99% of the amount.

HP5 column with FID detector was used for analysis. Detector temperature was set at 250° C.

The resultant product was characterized, and was found to be biochemically similar to the starting material, human frozen plasma.

This method of analysis is described by Kaliappanadar et al. in "Validation of a simple and sensitive gas chromatographic method of analysis of Tri-n-butyl phosphate from virally inactivated human Immunoglobulin" J. Chromatography B, 757:181-189 (1993).

Example 10

Analytical Procedures for Triton® and Tri-(N-Butyl) Phosphate (a) Product Specifications:

The product obtained for solvent-detergent treated pooled plasma employing the process of the present invention complies with the limits and specifications set forth in the British Pharmacopeia.

TABLE 7

| Tests | Limits | Batch1 | Batch2 |
|---|---|---|---|
| Antibodies to HIV-1 & HIV-2 | Absent | Absent | Absent |
| HCV | Absent | Absent | Absent |
| HbsAg | Absent | Absent | Absent |
| Ouchterlony test | Human origin | Complies | Complies |
| Osmolality | 240 mosmol/kg | Complies | Complies |
| Citrate | 25 mmol/L | 13.075 | 11.10 |
| Calcium | 5 mmol/L | 1.35 | 1.27 |
| Potassium | 5 mmol/L | 0.09 | 0.115 |
| Sodium | 200 mmol/L | 163 | 123.9 |
| Pyrogen | Rabbit test | Complies | Complies |
| Sterility | Should pass | Passes | Passes |
| TNBP | 2 ppm | 0 | 0.44 |
| Triton | 5 ppm | 1.2 | 0.59 |
| SDS-Page | Same bands | Complies | Complies |
| Haemaglutinin A&B | Group specific | B | O |
| PH | 6.5 to 7.6 | 6.9 | 7.3 |
| Total protein by Kjeldahl | Minimum 45 gm/Liter | 56 | 57.75 |
| Activated coagulation factors | ≧150 sec | 153 s | 155 s |
| Hepatitis A virus Ab | Minimum 2 IU/ml | Complies | Complies |
| Irregular erythrocytes | Absent | Complies | Complies |
| Factor VIII | ≧0.5 IU/ml | 0.623 | 0.712 |
| Factor V | ≧0.5 IU/ml | 0.98 | 1.02 |

All publications and patent applications cited in this specification are herein incorporated by reference in their entirety as if each individual publication or patent application were specifically and individually indicated to have been incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process of removing a tri-alkyl phosphate solvent and a polyoxyethylene ether detergent from a mixture of plasma, tri-alkyl phosphate solvent and polyoxyethylene ether detergent, wherein the solvent and the detergent have been used for viral inactivation of the plasma, the process comprising:
    treating the plasma in a batch mode with a polystyrene-divinylbenzene synthetic hydrophobic adsorbent in a ratio of 1 gm of adsorbent for 1 to 8 ml of plasma for 30-60 minutes at 20-30° C.; and
    collecting the treated plasma,
    wherein both the detergent and the solvent are removed in a single hydrophobic interaction treatment step.

2. The process of claim 1 wherein the polystyrene-divinylbenzene synthetic hydrophobic adsorbent is selected from the group consisting of DIAION® HP20, DIAION® HP20SS, SEPABEADS® SP825 and SEPABEADS® SP70.

3. The process of claim 1, wherein the method is employed on a pilot scale or employed on an industrial scale.

4. The process of claim 1, further wherein the synthetic hydrophobic adsorbent is regenerated following use.

5. The process of claim 1, wherein the treated plasma is substantially free of solvent-detergent.

6. The process of claim 5, wherein the treated plasma is substantially free from solvent-detergent and the composition of the plasma with respect to vital components of the plasma is not substantially altered.

7. The process of claim 1, wherein the treated plasma complies with the acceptable pharmacopeial limits of solvent less than 2 ppm and detergent less than 5 ppm.

8. The process of claim 1, wherein the virus inactivated by the solvent and detergent from the plasma is an enveloped virus.

9. The process of claim 8, wherein the virus is selected from the group consisting of a lipid-coated virus, HIV, hepatitis B, hepatitis C, cytomegalovirus, Epstein Barr virus, lactic dehydrogenase-elevating virus, arterivirus, a herpes group virus, a rhabdovirus, a leukovirus, a myxovirus, an alphavirus, Arbovirus (group B), a paramyxovirus, an arenavirus, and a coronavirus.

10. The process of claim 1, wherein the viral inactivated plasma is pooled from plasma of a plurality of donors.

11. A process of removing a tri-alkyl phosphate solvent and a polyoxyethylene ether detergent from a mixture of plasma, tri-alkyl phosphate solvent and polyoxyethylene ether detergent, wherein the solvent and the detergent have been used for viral inactivation of the plasma, the process comprising:
    treating the plasma in a column mode by running the plasma through a column of polystyrene-divinylbenzene synthetic hydrophobic adsorbent in a ratio of 1 gram adsorbent for 1 to 8 ml of plasma at a flow rate of 45-75 cm/hr at a temperature of 4-30° C.; and
    collecting the treated plasma,
    wherein both the detergent and the solvent are removed in a single hydrophobic interaction treatment step.

12. The process of claim 11 wherein the polystyrene-divinylbenzene synthetic hydrophobic adsorbent is selected from the group consisting of DIAION® HP20, DIAION® HP2055, SEPABEADS® SP825 and SEPABEADS SP70.

13. The process of claim 11, wherein the method is employed on a pilot scale or employed on an industrial scale.

14. The process of claim 11, further wherein the synthetic hydrophobic adsorbent is regenerated following use.

15. The process of claim 11, wherein the treated plasma is substantially free of solvent-detergent.

16. The process of claim 15, wherein the treated plasma is substantially free from solvent-detergent and the composition of the plasma with respect to vital components of the plasma is not substantially altered.

17. The process of claim 11, wherein the treated plasma complies with the acceptable pharmacopeial limits of solvent less than 2 ppm and detergent less than 5 ppm.

18. The process of claim 11, wherein the virus inactivated by the solvent and detergent from the plasma is an enveloped virus.

19. The process of claim 18, wherein the virus is selected from the group consisting of a lipid-coated virus, HIV, hepatitis B, hepatitis C, cytomegalovirus, Epstein Barr virus, lactic dehydrogenase-elevating virus, arterivirus, a herpes group virus, a rhabdovirus, a leukovirus, a myxovirus, an alphavirus, Arbovirus (group B), a paramyxovirus, an arenavirus, and a coronavirus.

20. The process of claim 11, wherein the virus inactivated plasma is pooled from plasma of a plurality of donors.

* * * * *

UNITED STATES PATENT AND TRADEMARK OFFICE
CERTIFICATE OF CORRECTION

PATENT NO. : 7,662,411 B2
APPLICATION NO. : 11/171877
DATED : February 16, 2010
INVENTOR(S) : Viswanathan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 521 days.

Signed and Sealed this

Thirtieth Day of November, 2010

David J. Kappos
*Director of the United States Patent and Trademark Office*